(12) United States Patent
Bastian

(10) Patent No.: US 7,938,833 B2
(45) Date of Patent: May 10, 2011

(54) ADJUSTABLE RESECTION GUIDE

(75) Inventor: Adam Bastian, Chester, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 989 days.

(21) Appl. No.: 11/599,152

(22) Filed: Nov. 14, 2006

(65) Prior Publication Data

US 2008/0114369 A1   May 15, 2008

(51) Int. Cl.
*A61B 17/90* (2006.01)
(52) U.S. Cl. .......................................... 606/87; 606/88
(58) Field of Classification Search ................ 606/86 R, 606/87–88, 96–98, 167–183; 623/18.11, 623/20.14–20.17, 20.21
See application file for complete search history.

(56) References Cited

U.S. PATENT DOCUMENTS

| | | | |
|---|---|---|---|
| 4,736,737 A | 4/1988 | Fargie et al. | |
| 4,935,023 A | 6/1990 | Whiteside et al. | |
| 5,002,545 A | 3/1991 | Whiteside et al. | |
| 5,234,433 A | 8/1993 | Bert et al. | |
| 5,275,603 A | 1/1994 | Ferrante et al. | |
| 5,342,368 A | 8/1994 | Petersen | |
| 5,364,401 A | 11/1994 | Ferrante et al. | |
| 5,417,694 A | 5/1995 | Marik et al. | |
| 5,451,228 A | 9/1995 | Johnson et al. | |
| 5,454,816 A * | 10/1995 | Ashby | 606/88 |
| 5,486,178 A | 1/1996 | Hodge | |
| 5,514,140 A | 5/1996 | Lackey | |
| 5,569,260 A | 10/1996 | Petersen | |
| 5,569,261 A | 10/1996 | Marik et al. | |
| 5,649,928 A | 7/1997 | Grundei et al. | |
| 5,662,656 A | 9/1997 | White | |
| 5,667,512 A | 9/1997 | Johnson | |
| 5,681,316 A * | 10/1997 | DeOrio et al. | 606/88 |
| 5,720,752 A | 2/1998 | Elliott et al. | |
| 5,776,137 A | 7/1998 | Katz | |
| 5,911,723 A | 6/1999 | Ashby et al. | |
| 5,916,219 A | 6/1999 | Matsuno et al. | |
| 5,916,220 A | 6/1999 | Masini | |
| 5,925,049 A | 7/1999 | Gustilo et al. | |
| 6,013,081 A | 1/2000 | Burkinshaw et al. | |
| 6,056,754 A | 5/2000 | Haines et al. | |
| 6,059,788 A | 5/2000 | Katz | |
| 6,077,270 A | 6/2000 | Katz | |
| 6,090,114 A * | 7/2000 | Matsuno et al. | 606/88 |
| 6,673,077 B1 | 1/2004 | Katz | |
| 6,740,092 B2 | 5/2004 | Lombardo et al. | |
| 6,780,180 B1 | 8/2004 | Goble et al. | |
| 6,814,735 B1 | 11/2004 | Zirngibl et al. | |
| 7,309,339 B2 * | 12/2007 | Cusick et al. | 606/88 |
| 2002/0133160 A1 * | 9/2002 | Axelson et al. | 606/88 |

(Continued)

*Primary Examiner* — Thomas C Barrett
*Assistant Examiner* — Larry E Waggle, Jr.
(74) *Attorney, Agent, or Firm* — Lerner, David, Littenberg, Krumholz & Mentlik, LLP

(57) ABSTRACT

A resection guide having an alignment barrel with holes that pass through the entire cross-section of the alignment barrel is disclosed. An alignment guide is mounted on the alignment barrel. Alignment guide can translate and rotate with respect to alignment barrel. The alignment guide has holes that extend through it. A resection plate is located at one end of the alignment guide. The resection plate has a resection surface. The resection guide is located on a bone using a navigation system and attached to the bone by driving two nails through the holes on the alignment barrel and one nail through one of the holes on the alignment guide. The resection surface is used to guide a tool for resecting the bone.

49 Claims, 4 Drawing Sheets

U.S. PATENT DOCUMENTS

| | | |
|---|---|---|
| 2002/0165552 A1 | 11/2002 | Duffner |
| 2002/0173797 A1 | 11/2002 | Van Zile et al. |
| 2003/0069585 A1 | 4/2003 | Axelson et al. |
| 2003/0212403 A1 | 11/2003 | Swanson |
| 2004/0015173 A1* | 1/2004 | Irving ........................ 606/88 |
| 2004/0039395 A1 | 2/2004 | Coon et al. |
| 2004/0039396 A1 | 2/2004 | Couture et al. |
| 2004/0153083 A1* | 8/2004 | Nemec et al. ............... 606/86 |
| 2004/0220583 A1 | 11/2004 | Pieczynski et al. |
| 2004/0260301 A1 | 12/2004 | Lionberger et al. |
| 2005/0004373 A1 | 1/2005 | Kumar et al. |
| 2005/0021039 A1 | 1/2005 | Cusick et al. |
| 2005/0049603 A1 | 3/2005 | Calton et al. |
| 2005/0055028 A1 | 3/2005 | Haines |
| 2005/0143746 A1 | 6/2005 | Steffensmeier et al. |
| 2005/0149037 A1 | 7/2005 | Steffensmeier et al. |
| 2005/0149039 A1 | 7/2005 | Haines et al. |
| 2005/0149040 A1 | 7/2005 | Haines et al. |
| 2005/0149041 A1 | 7/2005 | McGinley et al. |
| 2005/0154394 A1 | 7/2005 | Michalowicz |
| 2005/0171545 A1 | 8/2005 | Walsh et al. |
| 2005/0182415 A1 | 8/2005 | Steffensmeier et al. |
| 2005/0203528 A1 | 9/2005 | Couture et al. |
| 2005/0209598 A1 | 9/2005 | Grimm et al. |
| 2005/0209605 A1 | 9/2005 | Grimm et al. |
| 2005/0216032 A1 | 9/2005 | Hayden |
| 2005/0234465 A1 | 10/2005 | McCombs et al. |
| 2005/0234466 A1 | 10/2005 | Stallings |
| 2005/0240196 A1 | 10/2005 | Davis et al. |
| 2005/0256527 A1 | 11/2005 | Delfosse et al. |
| 2005/0261696 A1 | 11/2005 | Overes et al. |
| 2005/0273115 A1 | 12/2005 | Coon et al. |
| 2006/0004373 A1 | 1/2006 | Ondrla et al. |
| 2007/0208349 A1* | 9/2007 | Bastian et al. ............... 606/87 |

* cited by examiner

ADJUSTABLE RESECTION GUIDE

BACKGROUND OF THE INVENTION

The present invention relates to an apparatus for aligning medical instruments such as a cutting blade during a surgical procedure. More particularly, the present invention relates to an apparatus for aligning a resection guide for use in arthroplastic surgery of a patient's knee.

Arthroplasty is a known surgical procedure for replacing the knee joint which has been damaged due to disease or trauma. Total knee arthroplasty involves the replacement of portions of the patella, femur and tibia with artificial knee prostheses. In these prostheses, the articular surfaces of the bones are "resurfaced" with articular bearing components. One important aspect of these procedures is the correct resection of the bones. These resections must provide planes which are correctly angled in order to properly accept the prosthetic components.

Recently, various computerized navigation systems have been introduced to aid the practitioner during different surgical procedures. These systems include multiple video cameras which are deployed above the surgical site and a plurality of dynamic reference frame (DRF) devices, also known as trackers, which are attached to body parts and surgical instruments. The trackers can be LED devices or reflective spheres which are visible to the cameras. These trackers are attached to body parts and the surgical instruments and preferably include light emitting devices, such as light emitting diodes which are visible to the video cameras. The trackers communicate position information to a camera system located in the operating room. The camera system is connected to a computer which tracks the location of the tracker and the patient and displays the relationship on a CRT. Using software designed for a particular surgical procedure, a computer receiving input from the cameras guides the placement of surgical instruments such as cutting blocks for bone resection.

When using resurfacing type knee prostheses, the articular surface of the distal femur and proximal surface of the tibia are resurfaced with artificial knee components. Various apparatus are available to the surgeon for assisting in guiding a medical instrument such as a cutting blade for marking the femoral and tibial cuts which establish the desired resected surfaces. United States Patent Application Publication discloses one such apparatus for aligning the instruments during surgery. However, the disclosed apparatus is mechanically complex, and cumbersome and not intuitive to use. U.S. Pat. No. 5,681,316 is another example of a resection guide that is complex, cumbersome and not intuitive to use. Thus there is a need for a simple, easy to use and intuitive adjustable resection guide for aligning medical instruments during surgery.

SUMMARY OF THE INVENTION

The present invention overcomes the deficiencies of the prior art and provides a resection guide that is very simple in construction and simple and intuitive to use. The resection guide of the present invention has an alignment barrel having holes that pass through the entire cross-section of the alignment barrel. The longitudinal axis of at least two of the holes may be angled with respect to each other. By making the holes angled with respect to each other, locking of resection guide is enhanced. The alignment barrel also has a section that is of smaller cross section than the rest of the alignment barrel.

An alignment guide is mounted on the alignment barrel. The alignment guide may be mounted on the smaller section. The alignment guide can translate and rotate with respect to the alignment barrel. The alignment guide has holes that extend through it. The holes may be in a single row or may form more than one row or may be staggered. The holes are at a fixed distance from each other, for example, each hole is spaced 2 millimeters from the hole or holes next to it. The holes on the alignment barrel and the alignment guide are sized to allow a pin or a nail to be inserted through them. A resection plate is located at one end of the alignment guide.

The resection plate has a resection surface and a back surface. The resection plate has a wall extending from the back surface. The wall surrounds an opening that passes through resection plate. A tracker may be mounted in the opening.

In use, the resection guide is mounted on appropriate surface of a bone, for example, a distal femur as shown in FIG. 1. The resection guide is placed on the anterior surface of the distal femur using a navigation system that detects the tracker to locate the resection guide in three-dimensional space. The resection surface, after it is located and fixed in correct position, is used to guide the blade of the resection tool.

Once the resection guide is properly located on the anterior surface of the femur, a nail or bone pin is driven through one of the holes on the alignment barrel. The nail attaches the resection guide to the bone and fixes the resection surface in the medial-lateral direction and stops rotation of the resection surface so as to fix the internal-external rotation angle of the resection surface. However, at this time, the resection surface is not fixed in two planes, i.e., the resection surface can translate back and forth in the distal-proximal direction and it can also translate up and down along the length of the nail. Additionally, the resection surface can rotate around the nail and also around the alignment barrel.

Next, using the navigation system, the resection surface is positioned in position corresponding to correct varus/valgus rotation and a second nail is driven through another hole on the alignment barrel locking in the varus/valgus rotation. At this time, the resection surface is free to translate in the distal-proximal direction and rotate around the alignment barrel for adjustment of flexion-extension angle. Next, the resection surface is moved in distal-proximal direction to its correct position, and rotated to correct flexion-extension angle and a third nail is driven through one of the holes on the alignment guide. At this time, the resection surface is fixed in all three translational and all three rotational degrees of freedom. Next, the distal end of the bone is resected using the resection surface as a guide for the resection tool.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

DETAILED DESCRIPTION

Figure 1:
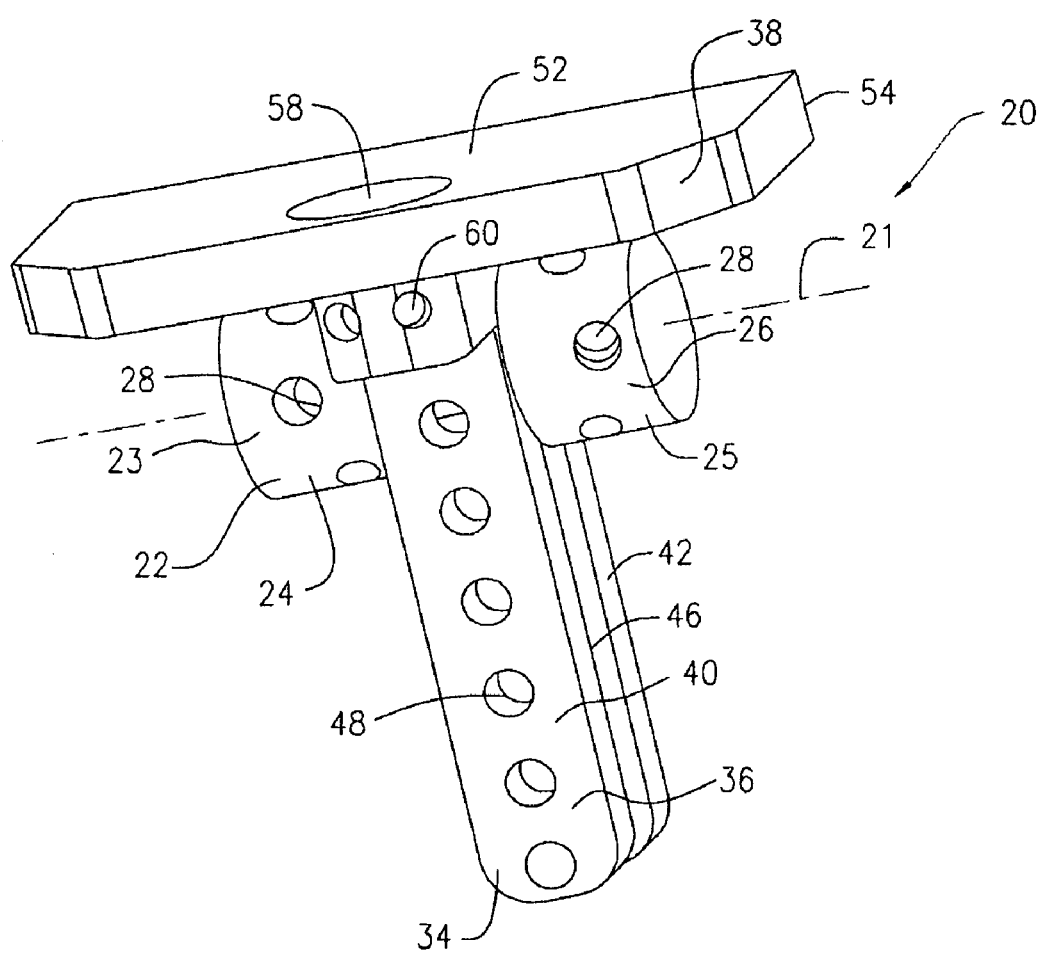
FIG. 1 shows a resection guide.
Figure 2:
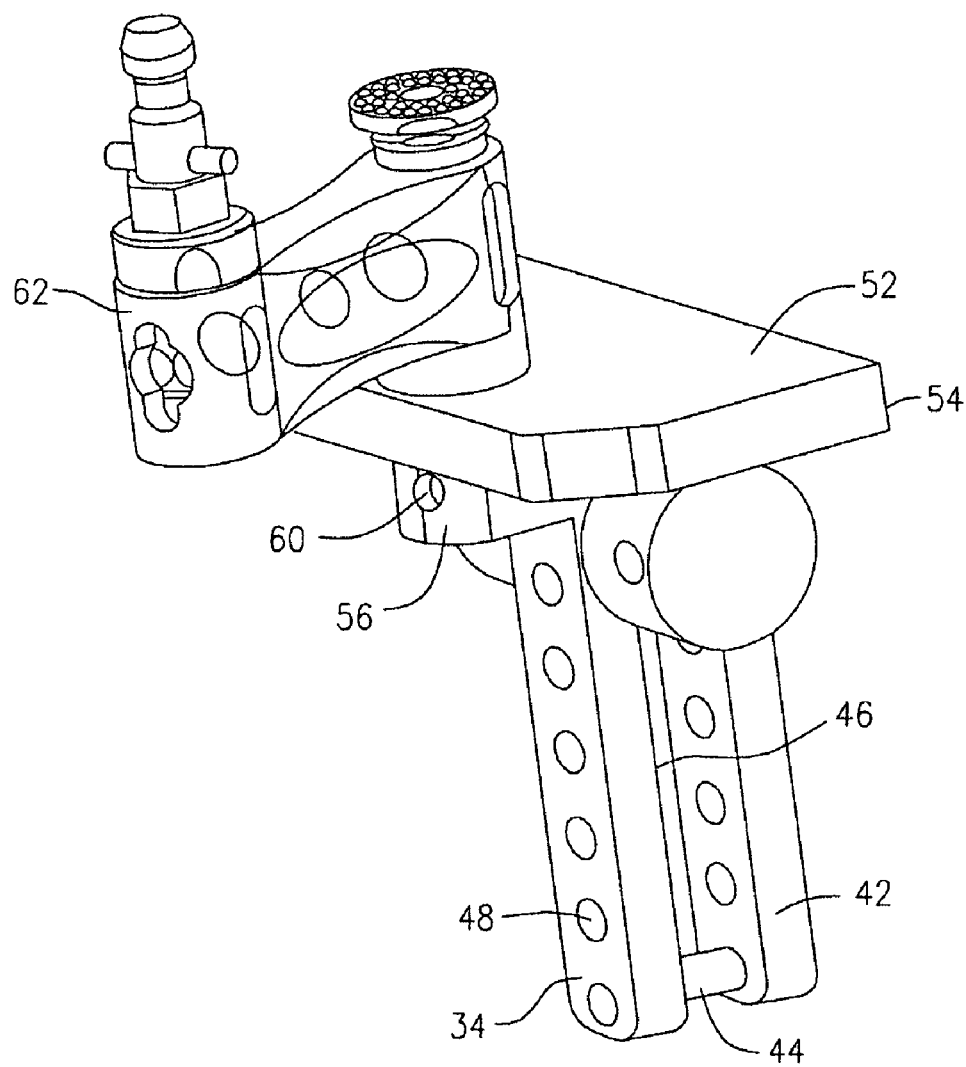
FIG. 2 shows the resection guide of FIG. 1 with a tracker attached to the resection guide.
Figure 3:
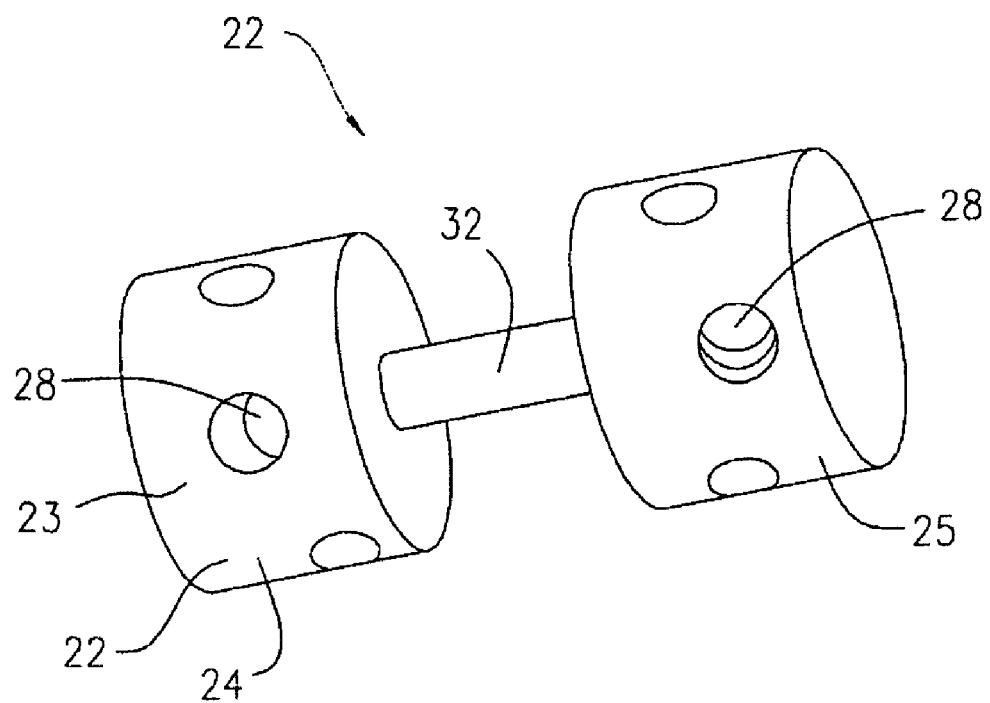
FIG. 3 shown the alignment barrel of FIG. 1.

FIGS. 1 and 2 show a resection guide 20. Resection guide 20 has an alignment barrel 22. In the preferred embodiment, alignment barrel 22 has a circular cross-section and a central longitudinal axis 21 running therethrough. Alignment barrel 22 may have different cross-sections, for example, an oval or rectilinear cross-section. Alignment barrel 22 has sections 23 and 25. Section 23 has surface 24 and section 25 has surface 26. Surfaces 24, 26 have holes 28. Holes 28 pass through the entire cross-section of alignment barrel 22. Each one of surfaces 24 and 26 can have one or more holes 28. Holes 28 on each one of surfaces 24 and 26 may be aligned with each other or may be staggered. The longitudinal axis of holes on surface 24 and holes on surface 26 may be angled with respect to each other. The typical angle between the longitudinal axis of holes on surface 24 and holes on surface 26 may be ten degrees. By making the holes 28 angled with respect to each other, locking of resection guide 20 to a bone is enhanced. Surface 24 may have two rows of holes 28. Similarly, surface 26 may also have two rows of holes 28. Holes 28 on surface 24 are located at a fixed distance from each other. Similarly, holes 28 on surface 26 are also located at a fixed distance from each other. Referring to FIG. 3, alignment barrel 22 has a section 32 connecting sections 23 and 25. As noted previously, sections 23, 25, 32 may be of an appropriate cross-section such as circular, oval, or rectilinear cross-section. Section 32 may be smaller compared to sections 23 and 25.

An alignment guide 34 is mounted on alignment barrel 22. Alignment guide 34 may be mounted on section 32. Alignment guide 34 can translate and rotate with respect to alignment barrel 22. Alignment guide 34 has a rail 36 attached to a resection surface 38. Rail 36 may be attached to resection plate 38 at a right angle. Rail 36 has an upper section 40 and lower section 42 connected by a middle section 44. A slot 46 is formed in middle section 44. Slot 46 can house middle section 32 of alignment barrel 22, thereby allowing the alignment guide 34 to rotate and translate around alignment barrel 22. However, alignment guide 34 may be mounted on alignment barrel 22 in any manner that allows alignment. guide 34 to translate and rotate with respect to alignment barrel 22. Alignment guide 34 has holes 48 that extend through it. Holes 48 may be in a single row or may form more than one row or may be staggered. Holes 48 are at a fixed distance from each other, for example, each hole 48 is spaced 2 millimeters from the hole or holes next to it. Holes 28 and 48 (FIG. 1) are sized to allow a pin or nail to be inserted through them.

Resection plate 38 has a resection plane or surface 52 and a back surface 54 proximally facing when guide 20 is mounted on the anterior femur. Resection plate 38 can be of any appropriate shape, for example, rectilinear shape. Resection plate 38 has a wall 56 extending from back surface 54. Wall 56 surrounds an opening 58 that passes through resection plate 38. Wall 56 has one or more smaller openings 60. The axis of openings 60 are at on angle, for example, 90° angle, to the axis of opening 58. In use, a tracker 62 may be mounted in hole 58. The portion of tracker 62 that snaps into opening 58 has balls on its surface. These balls snap into openings 60 to provide a firm seating for tracker 62 in the opening 58. Tracker 62 may be mounted using any other appropriate structure formed on the resection guide 20. For example, tracker 62 may be mounted in a groove or on a beam of appropriate cross-section. Tracker 62 can be used with a navigation system to locate resection guide 20 on the bone. However, resection guide 20 can be used without the aid of a navigation system. For example, resection guide 20 may be used with intermedullary or extramedullary alignment devices.

In use, resection guide 20 is mounted on appropriate surface of a bone, for example, the anterior surface of a femur. Resection guide 20 is placed on the bone using a navigation system that detects tracker 62 to locate resection guide 20 in three-dimensional space. The navigation system has software specific to the procedure being performed. The software ensures proper location of the resection guide 20. However, the surgeon can override the location of resection guide 20, as determined by the navigation system. Thus, the surgeon can locate resection guide 20 or resection surface 52 or both in a location he deems appropriate. Resection surface 52, after it is located and fixed in correct position, is used to guide the blade of the resection tool such as an oscillating saw blade 60 (FIG. 4).

Figure 4:
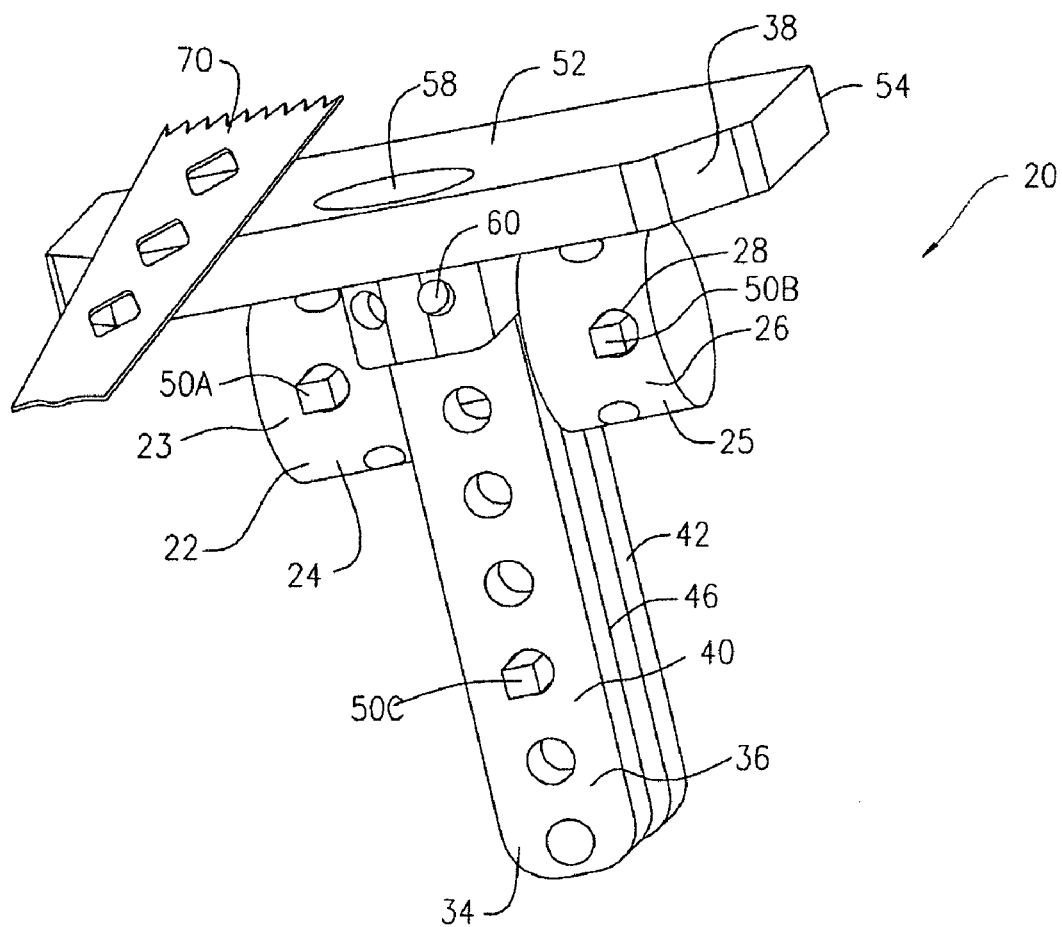
FIG. 4 shows the resection guide of FIG. 1 with a tool and nails positioned thereon.

Referring to FIG. 4, once resection guide 20 is properly located on the anterior surface of the bone, a nail 50A is driven through one of the holes 28 on surface 23. Nail 50A attaches resection guide 20 to the bone and fixes resection surface 52 in a medial-lateral direction and stops rotation of resection surface 52 so as to fix the internal-external rotation angle of resection surface 52. However, at this time, resection surface 52 is not fixed in two planes, i.e., resection surface 52 can translate back and forth in distal-proximal direction and it can also translate up and down along the length of nail 50A. Additionally, resection surface 52 can rotate around nail 50A and also around alignment barrel 22.

Next, using the navigation system, resection surface 52 is positioned in position corresponding to correct varus/valgus rotation and a second nail 50B is driven through hole 28 on surface 26 and into the bone. At this time, resection surface 52 is free to translate in distal-proximal direction and rotate around alignment barrel 22 for adjustment of flexion-extension angle. Next, resection surface 52 is moved in distal-proximal direction to its correct position, and rotated to correct flexion-extension angle and a third nail 50C is driven through one of the holes 48. At this time, resection surface 52 is fixed in all three translational and all three rotational degrees of freedom. Next, the distal end of the bone is resected using resection surface. 52 as a guide for the resection tool.

In the above description, resection guide 20 is mounted on the anterior surface of the bone. Alternatively, resection guide 20 may be mounted medially or laterally for resection of the distal end of the bone.

Although the invention herein has been described with reference to particular embodiments, it is to be understood that these embodiments are merely illustrative of the principles and applications of the present invention. For example, the above description is for distal resection of a femur; however, resection guide 20 may also be used for resection of other bones, such as, for distal resection of tibia. It is therefore to be understood that numerous modifications may be made to the illustrative embodiments and that other arrangements may be devised without departing from the spirit and scope of the present invention as defined by the appended claims.

The invention claimed is:

1. A resection guide comprising:
   an alignment barrel having a pair of first surfaces and a second surface positioned between the pair of first surfaces, the first surfaces each having a first diameter and the second surface having a second diameter smaller than the first diameter;
   at least a first hole and a second hole formed on the alignment barrel;

an alignment guide rotatably and slidably mounted on the alignment barrel, the alignment guide mounted on the second surface;
at least a third hole formed on the alignment guide; and
a resection plane located at one end of the alignment guide, the resection plane being capable of guiding a tool for resecting an end of a bone, wherein the resection plane may be translated in two planes and rotated around two axis after the resection guide is attached to the bone through one of the first or the second hole.

2. The resection guide of claim 1, wherein the axis of the first hole and the second hole are angled with respect to each other.

3. The resection guide of claim 1, further comprising:
a plurality of the first holes; and
a plurality of the second holes;
wherein the set of first holes and the set of second holes form a matched set of holes, and wherein each matched set of the first hole and the second hole is spaced a fixed distance from each other.

4. The resection guide of claim 3, further comprising:
a plurality of the third holes are formed on the alignment guide, the holes formed on the alignment guide being spaced a fixed distance from each other.

5. The resection guide of claim 4, wherein once the resection guide is attached to the bone, the resection plane can be moved in fixed increment without attachment at a different location.

6. The resection guide of claim 4, further comprising:
a mounting means formed on the resection plane.

7. The resection guide of claim 6, wherein the mounting means is an opening.

8. A resection guide comprising:
an alignment barrel having a first diameter and a second diameter, the barrel having a central longitudinal axis extending through a length of the alignment barrel, a first surface formed on the alignment barrel, the first surface having the first diameter, and a plurality of holes located on the first surface;
an alignment guide rotatably and slidably mounted on the second diameter portion of the alignment barrel, a second surface formed on the alignment guide;
a resection plane parallel to the central longitudinal axis, the resection plane located at one end of the alignment guide, the resection plane being capable of guiding a tool for resecting an end of a bone; and
a plurality of holes located on the second surface of the alignment guide.

9. The resection guide of claim 8, wherein the holes located on the second surface are spaced a fixed distance from each other.

10. The resection guide of claim 9, wherein once the resection guide is attached to the bone, the resection plane can be moved in medial-lateral and distal-proximal direction in fixed increment without reattachment at a different location.

11. The resection guide of claim 9, further comprising:
a mounting means formed on the resection plane.

12. The resection guide of claim 11, wherein the mounting means is an opening.

13. A bone resection system comprising:
an alignment barrel;
at least a first hole and a second hole formed on the alignment barrel;
an alignment guide rotatably and slidably mounted on the alignment barrel;
at least one hole formed on the alignment guide;
a resection plane located at one end of the alignment guide, the resection plane being capable of guiding a tool for resecting an end of a bone;
a first pin, the first pin when driven through the first hole on the alignment barrel stopping the movement of the resection plane in the medial-lateral direction and stopping the rotation of the resection plane so that the internal-external rotation angle of the resection plane is fixed;
a second pin, the second pin when driven through the second hole stopping the rotation of the resection plane so as to fix the Varus-Valgus angle of the resection plane without fixing the flexion-extension angle of the resection plane; and
a third pin, the third pin when driven through the hole on the alignment guide stopping the movement of the resection plane in the distal-proximal direction and stopping the rotation of the resection plane so that the flexion-extension angle of the resection plane is fixed.

14. The bone resection system of claim 13, further comprising:
a first surface formed on the alignment barrel, the first surface having a first diameter; and
a second surface formed on the alignment barrel, the second surface having a second diameter, the second diameter being smaller than the first diameter.

15. The bone resection system of claim 14, wherein the alignment guide is mounted on the second surface formed on the alignment barrel.

16. The bone resection system of claim 13, wherein the axis of the first hole and the second hole are angled with respect to each other.

17. The bone resection system of claim 13, further comprising:
a plurality of the first holes; and
a plurality of second holes;
wherein the set of first holes and the set of second holes formed a matched set of holes, and wherein each matched set of the first hole and the second hold is spaced a fixed distance from each other.

18. The bone resection system of claim 17, further comprising:
a plurality of the third holes formed on the alignment guide, the holes formed on the alignment guide being spaced a fixed distance from each other.

19. The bone resection system of claim 18, wherein, once the resection system is attached to the bone, the resection plane can be moved in fixed increment without attachment at a different location.

20. The bone resection system of claim 18, further comprising:
a mounting means formed on the resection plane.

21. The bone resection system of claim 20, wherein the mounting means is an opening.

22. A resection guide comprising:
an alignment barrel having a first diameter, a second diameter, a pair of first surfaces formed on the alignment barrel, and a second surface intermediate the pair of first surfaces, the pair of first surface having the first diameter and the second surface having the second diameter;
an alignment guide rotatably and slidably mounted on the second surface of the alignment barrel; and
a resection plane located at one end of the alignment guide, the resection plane being located on the bone with respect to three rotational degrees of freedom and three translational degrees of freedom by attaching the alignment barrel and the alignment guide to the bone.

23. The resection guide of claim 22, wherein the first diameter is larger than the second diameter.

24. The resection guide of claim 22, further comprising a plurality of holes located on the first surfaces.

25. The resection guide of claim 24, wherein the axis of at least two of the holes on the first surfaces are angled with respect to each other.

26. The resection guide of claim 24, wherein the holes located on the first surfaces are spaced a fixed distance from each other.

27. The resection guide of claim 26, further comprising a plurality of holes located on the second surface.

28. The resection guide of claim 27, wherein the holes located on the second surface are spaced a fixed distance from each other.

29. The resection guide of claim 28, wherein, once the resection guide is attached to the bone, the resection plane can be moved in a proximal-distal direction or a medial-lateral direction or both the proximal-distal and medial-lateral directions in fixed increment without reattachment on the bone at a different location.

30. The resection guide of claim 28, further comprising: a mounting means formed on the resection plane.

31. The resection guide of claim 30, wherein the mounting means is an opening.

32. A resection guide comprising:
an alignment barrel having a first diameter, a second diameter, and a central longitudinal axis extending through a length of the alignment barrel;
a first set of holes formed on the alignment barrel, the holes in the first set of holes being spaced at a fixed distance from each other;
an alignment guide rotatably and slidably mounted on the alignment barrel;
a second set of holes formed on the alignment guide, the holes in the second set of holes being spaced at a fixed distance from each other; and
a resection plane located at one end of the alignment guide, the resection plane being parallel to the central longitudinal axis and capable of guiding a tool for resecting an end of a bone, wherein, once the resection guide is attached to the bone, the resection plane can be moved in fixed increments in a distal-proximal direction or a medial-lateral direction or both the distal-proximal and the medial-lateral directions without reattachment at a different location.

33. The resection guide of claim 32, further comprising:
a first surface formed on the alignment barrel, the first surface having a first diameter; and
a second surface formed on the alignment barrel, the second surface having a second diameter, the second diameter being smaller than the first diameter.

34. The resection guide of claim 33, wherein the alignment guide is mounted on the second surface formed on the alignment barrel.

35. The resection guide of claim 32, wherein the axis of at least two holes from the first set of holes are angled with respect to each other.

36. The resection guide of claim 34, further comprising: a mounting means formed on the resection plane.

37. The resection guide of claim 36, wherein the mounting means is an opening.

38. A bone resection system comprising:
an alignment barrel;
at least a first hole and a second hole formed on the alignment barrel;
an alignment guide rotatably and slidably mounted on the alignment barrel;
at least one hole formed on the alignment guide;
a resection plane located at one end of the alignment guide, the resection plane being capable of guiding a tool for resecting an end of a bone;
a first pin, the fist pin when driven through the first hole on the alignment barrel stopping the movement of the resection plane in the anterior-posterior -direction and stopping the rotation of the resection plane so that the internal-external rotation angle of the resection plane is fixed;
a second pin, the second pin when driven through the second hole stopping the rotation of the resection plane so as to fix the flexion-extension angle of the resection plane without fixing the Varus-Valgus angle of the resection plane; and
a third pin, the third pin when driven through the hole on the alignment guide stopping the movement of the resection plane in the distal-proximal direction and stopping the rotation of the resection plane so that the Varus-Valgus -angle of the resection plane is fixed.

39. The bone resection system of claim 38, further comprising:
a first surface formed on the alignment barrel, the first surface having a first diameter; and
a second surface formed on the alignment barrel, the second surface having a second diameter, the second diameter being smaller than the first diameter.

40. The bone resection system of claim 39, wherein the alignment guide is mounted on the second surface formed on the alignment barrel.

41. The bone resection system of claim 38, wherein the axis of the first hole and the second hole are angled with respect to each other.

42. The bone resection system of claim 38, further comprising:
a plurality of the first holes; and
a plurality of second holes;
wherein the set of first holes and the set of second holes formed a matched set of holes, and wherein each matched set of the first hole and the second hold is spaced a fixed distance from each other.

43. The bone resection system of claim 42, further comprising:
a plurality of the third holes formed on the alignment guide, the holes formed on the alignment guide being spaced a fixed distance from each other.

44. The bone resection system of claim 43, wherein, once the resection system is attached to the bone, the resection plane can be moved in fixed increment without attachment at a different location.

45. The bone resection system of claim 43, further comprising:
a mounting means formed on the resection plane.

46. The bone resection system of claim 45, wherein the mounting means is an opening.

47. A resection guide comprising:
an alignment barrel having a first outer surface, a second outer surface, and a connecting surface intermediate the first and second surfaces, the first and second surfaces having a first diameter and the connecting surface having a second diameter smaller than the first diameter, and the barrel having a central longitudinal axis extending through a length of the alignment barrel;

an alignment guide rotatably and slidably mounted on the second diameter portion of the alignment barrel; and a resection plane parallel to the central longitudinal axis, the resection plane located at one end of the alignment guide, the resection plane being capable of guiding a tool for resecting an end of a bone.

48. The resection guide of claim 47, wherein the alignment guide is positioned on the second surface.

49. The system of claim 14, further including a third surface having a third diameter, wherein the second surface is intermediate the first and third surfaces, and the second diameter is smaller than the third diameter, and wherein the alignment guide is mounted on the second surface formed on the alignment barrel.

* * * * *